United States Patent [19]

Gleason et al.

[11] 3,994,954

[45] Nov. 30, 1976

[54] PROCESS FOR PREPARING SUBSTITUTED GLYCINES

[75] Inventors: John G. Gleason, Cornwall Heights, Pa.; Kenneth G. Holden, Haddonfield, N.J.; Nelson C. F. Yim, Philadelphia, Pa.

[73] Assignee: SmithKline Corporation, Philadelphia, Pa.

[22] Filed: June 24, 1975

[21] Appl. No.: 589,962

Related U.S. Application Data

[62] Division of Ser. No. 447,468, Feb. 28, 1974, Pat. No. 3,920,730.

[52] U.S. Cl. .................. 260/471 C; 260/308 D; 260/326.12 R; 260/332.2 A; 260/326.14 R; 260/347.5; 260/252; 260/302 D; 260/455 A; 260/307 G; 260/473 F; 260/473 R; 260/477
[51] Int. Cl.² .................................. C07C 155/02
[58] Field of Search ....... 260/307 R, 308, 326.12 R, 260/326.14, 332.2, 347.5, 455 A, 471 C, 473, 477

[56] References Cited

UNITED STATES PATENTS 3,920,730   11/1975   Gleason et al. ................ 260/455 A

OTHER PUBLICATIONS

Org. Chem., Chap. 29 (1975), pp. 934–1016.
Basic Principles of Org. Chem. (1965), pp. 979–996, Chap. 27.

*Primary Examiner*—Lewis Gotts
*Assistant Examiner*—D. R. Phillips
*Attorney, Agent, or Firm*—Janice E. Williams; William H. Edgerton; Alan D. Lourie

[57] ABSTRACT

A new process is disclosed for the preparation of N-acyl-α-aromatic and N-acyl-α-heteroaromatic glycines by reaction of an α-ester or ether of an N-acylglycine ester or acid with an aromatic or heteroaromatic compound. Also disclosed are new intermediates for preparing N-acyl-α-aromatic and N-acyl-α-heteroaromatic glycines.

8 Claims, No Drawings

PROCESS FOR PREPARING SUBSTITUTED GLYCINES

This is a division of application Ser. No. 447,468, filed Feb. 28, 1974, now U.S. Pat. No. 3,920,730.

This invention relates to a process for preparing N-acyl-α-aromatic and N-acyl-α-heteroaromatic glycines and to intermediates for preparing said compounds. In particular, the invention relates to a process for preparing compounds of formula III by reacting an α-ester or ether of an N-acylglycine ester or acid (I) with an aromatic or heteroaromatic compound (II).

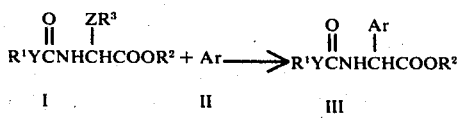

In the above formulas I–III, $R^1Y$ is any group which with the adjacent carbonyl group forms an amine protective group removable under conditions which are mild enough not to affect the remainder of the molecule. $R^1$ can therefore be straight or branched chain lower alkyl of one to four carbon atoms, $\beta,\beta,\beta$-trichloroethyl or substituted or unsubstituted benzyl. Y can be O or S. The substituents on benzyl can be halo, alkyl, alkoxy or nitro. Preferred groups are those where $R^1Y$ is t-butoxy, $\beta,\beta,\beta$-trichloroethoxy and benzyloxy.

$ZR^3$ is any ester or ether group readily replaceable by an electron-rich aromatic or heteroaromatic group. Z can therefore be O, S or

and $R^3$ can be straight or branched chain lower alkyl of one to four carbon atoms; halomethyl such as trifluoromethyl; aryl such as phenyl, which may be unsubstituted or substituted with one or two halo, lower alkyl, hydroxy, lower alkoxy, nitro, amino or acetamido groups; or aralkyl such as benzyl, which may be unsubstituted or substituted in the same manner as phenyl. Preferred groups are those where $ZR^3$ is lower alkanoyloxy such as

(acetoxy), lower alkoxy such as $OCH_3$ (methoxy) and $OC_4H_9$ (butoxy), $SCH_2C_6H_5$ (benzylthio), $OC_6H_5$ (phenoxy) and lower alkylthio such as $SCH_3$ (methylthio).

$R^2$ is hydrogen, except when $ZR^3$ is phenoxy, or any carboxyl protective group which is easily removable or is itself usable in the acylation reaction in which the product glycine compound is used. $R^2$ can therefore be hydrogen, except when $ZR^3$ is phenoxy, straight or branched chain lower alkyl of one to four carbon atoms, haloalkyl such as $\beta,\beta,\beta$-trichloroethyl, benzyl or substituted benzyl such as p-nitrobenzyl or p-methoxybenzyl. In addition, $R^2$ can be any activated ester known to the art to be usable for the acylation of peptides, penicillins or cephalosporins.

Ar can be any aromatic or heteroaromatic group that is sufficiently electron-rich to replace the $ZR^3$ group. Ar can be phenyl, thienyl, furyl, pyrryl, naphthyl, indolyl, purinyl, tetrazolyl, oxadiazolyl or thiadiazolyl. Ar can be unsubstituted or substituted with one or two lower alkyl, lower alkoxy, lower alkylthio, halo, hydroxy, mercapto, nitro or amino groups, or any other groups that do not by their reactivity or election-withdrawing character prevent the replacement reaction from proceeding satisfactorily. The only certain limitation on the nature of the Ar group is that it must possess an unsubstituted position which can bond to the α-carbon atom of the glycine molecule.

When used herein, the terms "lower alkyl", "lower alkoxy" and "lower alkanoyl" are intended to refer to straight or branched chain groups containing from one to four carbon atoms. The term "halo" is intended to refer to fluoro, chloro, bromo and iodo.

N-Acyl-α-aromatic and N-acyl-α-heteroaromatic glycines are intermediates useful for preparing antibacterial aromatic and heteroaromatic glycinamidopenicillins and cephalosporins. Examples of such antibacterial compounds are described in U.S. Pat. Nos. 2,985,648, 3,507,861 and 3,560,489 and Belgian Pat. No. 784,995. The penicillins and cephalosporins are prepared by acylation of the penicillin or cephalosporin nucleus with the aromatic or heteroaromatic glycine. Prior to the acylation reaction, the amino group of the glycine moiety is normally protected with any of a variety of well-known and easily-removed amine protective groups. Thus, one normally must prepare the aromatic or heteroaromatic glycine compound and then protect the amino group prior to the acylation reaction. The advantage of the present process is that the protection of the amino group can be accomplished in the same reaction in which the aromatic or heteroaromatic glycine is itself prepared.

The process of this invention whereby the $ZR^3$ leaving group is replaced by the Ar group is carried out by combining the α-ester or ether of formula I with at least an equimolar amount of the aromatic or heteroaromatic compound (Ar). The reaction is generally carried out using an acid catalyst, including Lewis acids, among which boron trifluoride as its etherate, aluminum chloride, formic acid and trifluoroacetic acid are preferred. Highly election-rich aromatic reactants such as indole, purine anbd pyrrole require no catalyst. When the aromatic moiety is insufficiently election-rich to replace the α-ester or ether, even with an acid catalyst, it is used as a metal salt. Thus, when Ar is phenyl, the reaction is best carried out using phenyl lithium as a reactant. When the leaving group ($ZR^3$) is a thioether, mercuric acetate is used in addition to the acid catalyst.

The reaction is carried out in the liquid phase. A solvent is generally preferred; among those being usable are such non-polar organic solvents as benzene, toluene, xylene, carbon tetrachloride, ethyl acetate, dioxane, tetrahydrofuran, ether, methylene chloride and chloroform. The aromatic reactant may be employed in large excess and thus itself serve as the solvent. The temperature of the reaction will depend upon the nature of the reactants. When the aromatic moiety is especially sensitive or reactive, the temperature should be kept low, in the case of phenyl lithium and furan, as low as −78° C. Otherwise, the temperature should be approximately between 0° C and ambient temperature (ca 25° C) and the reaction should be allowed to proceed until it is substantially complete, as indicated by thin layer chromatography. This time will vary from approximately 15 minutes to 24 hours. In cases where an aromatic moiety is sluggish in reacting, high temperatures, including those reached only by heating in the absence of solvent, may be required. The product is then isolated and purified according to standard methods, including solvent extraction, chromatography and recrystallization.

The esters of formula III obtained by this process may be hydrolyzed or used directly in acylating penicillin and cephalosporin intermediates by well-known methods. Use of a base such as sodium bicarbonate or sodium carbonate in aqueous methanol or dioxane is preferred for hydrolysis.

The compounds of formula I which are reacted with the aromatic nuclei to give compounds of formula III are themselves prepared by condensing an amide of formula IV, a glyoxylic ester of formula V and an acid, alcohol or mercaptan of formula VI, as shown below:

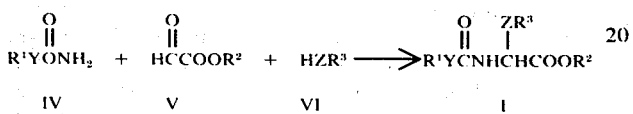

An anhydride may be used instead of an acid. $R^1, R^2, R^3, Y$ and $Z$ are as defined above. This reaction is carried out either using one of the reactants as a solvent or in an organic solvent such as dioxane, benzene, xylene or toluene. The temperature of the reaction will vary with the reactants, but it is preferable to carry it out at the reflux temperature of the solvent unless lower temperatures are necessary to prevent serious decomposition.

Compounds of formula I where $ZR^3$ is acyloxy are new and are considered part of the present invention. Among the preferred compounds of this group are those where $R^1Y$ is t-butoxy, $\beta,\beta,\beta$-trichloroethoxy or benzyloxy; $R^2$ is hydrogen or lower alkyl and $ZR^3$ is lower alkanoyloxy. The p-nitrobenzyl and p-methoxybenzyl glyoxylic acid esters are prepared according to known procedures, for example, by treating glyoxylic acid with a p-nitrobenzyl or p-methoxybenzyl halide in the presence of base.

It will be recognized that, due to the asymmetric $\alpha$-carbon atom in the glycine compounds of formulas I and III, optical isomers will exist. The resolved glycines are readily obtained, when desired, by resolution of the racemic compounds by well-known methods including fractional crystallization of a salt formed with an optically active acid or base. Both the resolved and racemic compounds are usable and obtainable in the process of the invention and both are comprehended by the definition of the claimed intermediates glycines.

Many examples of $\alpha$-substituted N-acylglycines and glycine esters are found in the prior art. Various $\alpha$-alkoxy-N-benzoylglycines and glycine esters are described in Zhur. Obshch. Khim., 25, 1360 (1955), Bull. Soc. Chim. Fr., 530 (1959), Doklady Akad. Nauk. S.S.S.R., 106,675 (1956) and 137, 1377 (1961) and Nippon Kagaku Zasshi, 76, 1022 (1955). N-Phenylacetyl-$\alpha$-methoxyglycine is disclosed in U.S. Patent 2,523,621, while N-phenylacetyl-$\alpha$-benzyloxyglycine is described in Experientia, 21, 317 (1965). The corresponding methyl and benzyl esters are found in J. Chem. Soc. C, 14, 1264 (1967) and Ann. Chim. (Rome), 60, 259 (1970), respectively.

Huisgen and Blaschke have prepared N-ethoxycarbonyl-$\alpha$-benzoylglycine ethyl ester [Chem. Ber., 98, 29585 (1965)]. The preparations of $\alpha$-hydroxy, $\alpha$-amino (for example, unsubstituted and substituted anilino, benzylamino and morpholino) and $\alpha$-halo N-ethoxycarbonyl, N-benzoyl and N-phenylacetylglycine esters are described by Matthies[Pharmazie, 25, 522 (1970)].

Synthesis of N-$\alpha$-alkoxybenzylbenzamides is described in Tetrahedron, 23, 2869–77 (1967). Synthesis of an $\alpha$-carbethoxyiminoacetic ester and conversion to an N-acyl-$\alpha$-indolylglycine ester are described in Tetrahedron Letters No. 41, 4371–73 (1968). Synthesis of glycines by means of a Grignard reaction is described in Tetrahedron Letters No. 21, 1813–16 (1970).

Other references may exist describing compounds similar to those described in the above references. However, the inventors are aware of no disclosure of N-acyl-$\alpha$-acyloxyglycines or of their use in preparing N-acyl-$\alpha$-aromatic or heteroaromatic glycines.

The following examples illustrate the products and processes of the invention, but are not to be construed as limiting the scope thereof. Temperatures are in degrees Centigrade unless otherwise stated.

EXAMPLE 1

N-t-Butoxycarbonyl-2-acetoxyglycine n-butyl ester

A solution of 23.4 g (0.2 mol.) of t-butyl carbamate [Org. Syn., 48, 32 (1968); U.S. 3,072,710] and 32.2 g. (0.25 mol.) of n-butyl glyoxylate (Org. Syn. Col. Vol. 4, 124) in 150 ml. of acetic anhydride was refluxed for 1.25 hours. The reaction mixture was then cooled, the solvent was removed in vacuo and the residue was molecularly distilled at 130°/.05 mm. to give the title compound.

Use of formic, propionic or butyric anhydride in place of the acetic anhydride gives the corresponding 2-formyloxy, 2-propionyloxy or 2-butyryloxy compound, respectively.

EXAMPLE 2

N-($\beta,\beta,\beta$-Trichloroethoxycarbonyl)-2-acetoxyglycine n-butyl ester

When 38.5 g. of $\beta,\beta,\beta$-trichloroethyl carbamate (U.S. 3,072,710) was substituted in the procedure of Example 1 for t-butyl carbamate, the title compound was obtained.

EXAMPLE 3

Substitution of 22.6 g. of benzyl carbamate in the procedure of Example 1 for t-butyl carbamate gave N-benzyloxycarbonyl-2-acetoxyglycine n-butyl ester.

By similar use of p-methoxybenzyl carbamate and p-nitrobenzyl carbamate in the procedures described herein, there are prepared the corresponding N-(p-methoxy- and p-nitrobenzyloxycarbonyl)glycines of this invention.

EXAMPLE 4

N-Benzyloxycarbonyl-2-n-butoxyglycine n-butyl ester

A solution of 3.0 g. (0.02 mol.) of benzyl carbamate, 1.8 g. (0.02 mol.) of glyoxylic acid hydrate and 0.1 g of p-toluenesulfonic acid in 50 ml. of n-butanol was slowly distilled over a one hour period. The last of the solvent was removed in vacuo to give a residue which was dissolved in hexane and filtered to remove the p-toluenesulfonic acid. The filtrate was chromatographed on alumina (Woelm, activity II) and eluted with hexane. Concentration of the eluate in vacuo and molecular distillation of the residue at 130°/0.1 mm. gave the title compound.

EXAMPLE 5

N-Benzyloxycarbonyl-2-methoxyglycine methyl ester

A solution of 3.0 g. (0.02 mol.) of benzyl carbamate and 1.8 g. (0.02 mol.) of glyoxylic acid hydrate in 50 ml. of 1:1 methanol-benzene containing 0.1 g. of p-toluenesulfonic acid was slowly distilled. During the course of the distillation the solvent was periodically replaced with 1:4 methanol-benzene to keep the total volume at least 20 ml. After 1 hour, the reaction mixture was concentrated in vacuo and the residue was dissolved in 10 ml. of benzene and filtered. The filtrate was chromatographed on alumina (Woelm, activity II) and eluted with benzene. Concentration of the eluate in vacuo gave the title compound, m.p. 74°–75° (benzene-hexane).

EXAMPLE 6

N-t-Butoxycarbonyl-2-phenoxyglycine n-butyl ester

To 2.9 g. (0.01 mol.) of N-t-butoxycarbonyl-2-acetoxyglycine n-butyl ester in 10 ml. of dioxane was added a solution of sodium phenolate prepared from 0.94 g. of phenol and 0.54 g. of sodium methoxide in 15 ml. of dioxane. After refluxing for 2 hours, the solvent was evaporated in vacuo and the residue was dissolved in ethyl acetate. The ethyl acetate solution was washed with cold 10% aqueous sodium hydroxide, dried ($MgSO_4$) and concentrated to yield the title compound as an oil.

Alternatively, N-t-Butoxycarbonyl-2-phenoxyglycine n-butyl ester was prepared by heating a mixture of 1.5 g. (0.005 mol.) of N-t-butoxycarbonyl-2-acetoxylglycine n-butyl ester and 0.5 g. (0.005 mol.) of phenol at 150° for 1 hour. The residue was dissolved in ethyl acetate and the resulting solution was washed with cold 10% aqueous sodium hydroxide, dried ($MgSO_4$) and concentrated to give the title compound.

EXAMPLE 7

N-Benzyloxycarbonyl-2-S-benzylthioglycine

A mixture of 15.1 g. (0.1 mol.) of benzyl carbamate, 7.4 g. (0.1 mol.) of glyoxylic acid hydrate and 24.0 g. (0.1 mol.) of benzyl mercaptan in 100 ml. of toluene was refluxed for 0.5 hour. After cooling, the reaction mixture was filtered and the crystalline product was washed with toluene, dried in vacuo and recrystallized from ethyl acetate-hexane to give the title compound, m.p. 120°–122°.

EXAMPLE 8

N-t-Butoxycarbonyl-2-S-methylthioglycine

When equivalent amounts of t-butyl carbamate and methyl mercaptan are substituted in the procedure of Example 7 for benzyl carbamate and benzyl mercaptan, respectively, the title compound is obtained.

EXAMPLE 9

When an equivalent amount of t-butyl thiocarbamate [J. Org. Chem. 28, 3421 (1963); U.S. Pat. No. 3,072,710] is substituted in the procedure of Example 1 for t-butyl carbamate, N-t-butylthiocarbonyl-2-acetoxyglycine n-butyl ester is obtained.

Similarly, substitution of an equivalent amount of benzyl thiocarbamate [J. Amer. Chem. Soc., 82, 4582 (1960)] in the procedure of Example 1 for t-butyl carbamate gives N-benzylthiocarbonyl-2-acetoxyglycine n-butyl ester.

EXAMPLE 10

N-Benzylthiocarbonyl-2-n-butoxyglycine n-butyl ester

When an equivalent amount of benzyl thiocarbamate is substituted in the procedure of Example 4 for benzyl carbamate, the title compound is obtained.

EXAMPLE 11

N-Benzylthiocarbonyl-2-methoxyglycine methyl ester

When an equivalent amount of benzyl thiocarbamate is substituted in the procedure of Example 5 for benzyl carbamate, the title compound is obtained.

EXAMPLE 12

N-t-butylthiocarbonyl-2-phenoxyglycine n-butyl ester

Substitution of an equivalent amount of N-t-butylthiocarbonyl-2-acetoxylglycine n-butyl ester in the procedure of Example 6 for N-t-butoxycarbonyl-2-acetoxyglycine n-butyl ester gives the title compound.

EXAMPLE 13

N-Benzylthiocarbonyl-2-S-benzylthioglycine

When an equivalent amount of benzyl thiocarbamate is substituted in the procedure of Example 7 for benzyl carbamate, the title compound is obtained.

EXAMPLE 14

N-t-Butylthiocarbonyl-2-S-methylthioglycine

Substitution of an equivalent amount of t-butyl thiocarbamate in the procedure of Example 8 for t-butyl carbamate gives the title compound.

EXAMPLE 15

N-Benzyloxycarbonyl-2-n-butoxyglycine

A solution of 0.002 mol. of N-benzyloxycarbonyl-2-n-butoxyglycine n-butyl ester is stirred with 10 ml. of methanol and 10 ml. of 5% aqueous sodium bicarbonate-sodium carbonate solution for five hours at 25°. The reaction mixture is then diluted with water and shaken with ethyl acetate. The layers are separated and the aqueous layer is acidified to pH 2.0 and extracted with ethyl acetate containing 10% ethanol. The extracts are dried ($Na_2SO_4$) and concentrated in vacuo to give the title compound.

In like manner, the other N-alkoxycarbonyl and N-alkylthiocarbonyl glycine esters described herein may be converted to the corresponding acids.

EXAMPLE 16

When an equivalent amount of methyl glyoxylate [Synthesis, 544 (1972)] is substituted in the procedure of Example 1 for n-butyl glyoxylate, N-t-butoxycarbonyl-2-acetoxyglycine methyl ester is obtained.

In like manner, N-($\beta,\beta,\beta$-trichloroethoxycarbonyl)-2-acetoxyglycine methyl ester is prepared by substitution of an equivalent amount of methyl glyoxylate in the procedure of Example 2 for n-butyl glyoxylate.

Similarly, substitution of an equivalent amount of methyl glyoxylate in the procedure of Example 3 for n-butyl glyoxylate gives N-benzyloxycarbonyl-2-acetoxyglycine methyl ester.

Other glycine methyl esters may be prepared by substitution of methyl glyoxylate for n-butyl glyoxylate in the appropriate procedures.

EXAMPLE 17

Substitution of an equivalent amount of ethyl glyoxylate [Synthesis, 544 (1972)] in the procedure of Example 1 for n-butyl glyoxylate gives N-t-butoxycarbonyl-2-acetoxyglycine ethyl ester.

In like manner, when an equivalent amount of ethyl glyoxylate is substituted in the procedure of Example 2 for n-butyl glyoxylate, N-($\beta,\beta,\beta$-trichloroethoxycarbonyl)2-acetoxyglycine ethyl ester is obtained.

When an equivalent amount of ethyl glyoxylate is substituted in the procedure of Example 3 for n-butyl glyoxylate, N-benzyloxycarbonyl-2-acetoxyglycine ethyl ester is obtained.

Other glycine ethyl estes may be similarly prepared by substitution of an equivalent amount of ethyl glyoxylate for n-butyl glyoxylate in the appropriate procedure.

EXAMPLE 18

When an equivalent amount of $\beta,\beta,\beta$-trichloroethyl glyoxylate [J. Amer. Chem. Soc., 88, 852 (1966)] is substituted in the procedure of Example 1 for n-butyl glyoxylate, N-t-butoxycarbonyl-2-acetoxyglycine $\beta,\beta,\beta$-trichloroethyl ester is obtained.

Similarly, substitution of an equivalent amount of $\beta,\beta,\beta$-trichloroethyl glyoxylate in the procedure of Example 2 for n-butyl glyoxylate gives N-($\beta,\beta,\beta$-trichloroethoxycarbonyl)-2-acetoxyglycine $\beta,\beta,\beta$-trichloroethyl ester.

In like manner, when an equivalent amount of $\beta,\beta,\beta$-trichloroethyl glyoxylate is substituted in the procedure of Example 3 for n-butyl glyoxylate, N-benzyloxycarbonyl-2-acetoxyglycine $\beta,\beta,\beta$-trichloroethyl ester is obtained.

Likewise, other glycine $\beta,\beta,\beta$-trichloroethyl esters may be prepared by substitution of an equivalent amount of $\beta,\beta,\beta$-trichloroethyl glyoxylate for n-butyl glyoxylate in the appropriate procedures.

EXAMPLE 19

Substitution of an equivalent amount of benzyl glyoxylate in the procedure of Example 1 for n-butyl glyoxylate gives N-t-butoxycarbonyl-2-acetoxyglycine benzyl ester.

In like manner, when an equivalent amount of benzyl glyoxylate is substituted in the procedure of Example 2 for n-butyl glyoxylate, N-($\beta,\beta,\beta$-trichloroethoxycarbonyl)-2-acetoxyglycine benzyl ester is obtained.

When an equivalent amount of benzyl glyoxylate is substituted in the procedure of Example 3 for n-butyl glyoxylate, N-benzyloxycarbonyl-2-acetoxyglycine benzyl ester is obtained.

Other glycine benzyl esters may be similarly prepared by substitution of an equivalent amount of benzyl glyoxylate for n-butyl glyoxylate in the appropriate procedure.

Similarly, use of p-methoxybenzyl glyoxylate or p-nitrobenzyl glyoxylate in place of benzyl glyoxylate in the above procedures gives the corresponding glycine p-methoxybenzyl and p-nitrobenzyl esters.

EXAMPLE 20

When an equivalent amount of N-t-butoxycarbonyl-2-acetoxyglycine methyl ester is substituted in the procedure of Example 6, N-t-butoxycarbonyl-2-phenoxyglycine methyl ester is obtained.

In like manner, N-t-butoxycarbonyl-2-phenoxyglycine ethyl ester is obtained by substitution of an equivalent amount of N-t-butoxycarbonyl-2-acetoxyglycine ethyl ester in the procedure of Example 6.

Similarly, when an equivalent amount of N-t-butoxycarbonyl-2-acetoxyglycine $\beta,\beta,\beta$-trichloroethyl ester is substituted in the procedure of Example 6, N-t-butoxycarbonyl-2-phenoxyglycine $\beta,\beta,\beta$-trichloroethyl ester is obtained.

EXAMPLE 21

N-t-Butoxycarbonyl-2-phenylglycine n-butyl ester

A solution containing 2.4 mmol. of phenyl lithium in benzene-ether was added dropwise at $-78°$ under argon to a solution of 700 mg. (2.4 mmol.) of N-t-butoxycarbonyl-2-acetoxyglycine n-butyl ester in 15 ml. of dry ether. The mixture was stirred for 2 hours at $-78°$, then for 1 hour at 25°. The mixture was diluted with water, the layers were separated and the ether layer was washed with water, dried ($Na_2SO_4$) and concentrated in vacuo. The residue was chromatographed on silica gel with methylene chloride to give a crude product which was rechromatographed on basic alumina to give the title compound.

Use of 2-formyloxy, 2-propionyloxy, or 2-butyryloxy starting materials gives the same product.

EXAMPLE 22

N-t-Butoxycarbonyl-2-(4-methoxyphenyl)glycine n-butyl ester

A solution of 290 mg. (1 mmol.) of N-t-butyoxycarbonyl-2-acetoxyglycine n-butyl ester, 0.5 ml. of anisole and 3 drops of boron trifluoride etherate in 5 ml. of methylene chloride was stirred at 25° for 4 hours. The solvent was removed and the residue was chromatographed on silica gel and eluted with 1:1 chloroform-hexane to give the title compound.

EXAMPLE 23

N-t-butoxycarbonyl-2-(2,4-dihydroxyphenyl)glycine

To a stirred mixture of 11.0 g. (0.1 mol.) of resorcinol and 24.7 g. (0.085 mol.) of N-t-butoxycarbonyl-2-acetoxyglycine n-butyl ester in 250 ml. of methylene chloride at 0° was added 1 ml. of boron trifluoride etherate. The reaction mixture was allowed to warm to room temperature during a 30 minute period, then it was stirred for an additional 3 hours. The reaction mixture was washed five times with equal volumes of water, dried ($Na_2SO_4$) and concentrated in vacuo to give N-t-butoxycarbonyl-2-(2,4-dihydroxyphenyl)glycine n-butyl ester.

To a boiling solution of 23 g. (0.067 mol.) of N-t-butoxycarbonyl-2-(2,4-dihydroxyphenyl)glycine n-butyl ester in 300 ml. of methanol was slowly added a solution of 23 g. of sodium bicarbonate in 300 ml. of water. During addition, the reaction mixture was kept under a nitrogen atmosphere and the methanol was allowed to distill from the mixture. When all the methanol had been distilled the mixture was cooled, adjusted to pH 7.0 with phosphoric acid and extracted with ethyl acetate. The aqueous phase was acidified to pH 4.0 and again extracted with ethyl acetate. The extract was dried (Na$_2$SO$_4$) and concentrated in vacuo to give the title compound.

EXAMPLE 24

N-t-Butoxycarbonyl-2-(3-acetamido-4-hydroxyphenyl)glycine and
N-t-butoxycarbonyl-2-(3-acetamido-2-hydroxyphenyl)glycine To a stirred mixture of 20.0 g. (0.069 mol.) of N-t-butoxycarbonyl-2-acetoxyglycine n-butyl ester, 11.5 g. (0.076 mol.) of 2-acetamidophenol and 200 ml. of methylene chloride was added 11.0 g. of boron trifluoride etherate under a nitrogen atmosphere. After 20 minutes the reaction mixture was shaken with sufficient aqueous sodium carbonate to bring the final pH of the aqueous phase to 7–8. The organic phase was dried (Na$_2$SO$_4$) and concentrated to give a residue which was hydrolyzed with sodium carbonate according to the procedure described in Example 23. The hydrolysis product, a mixture of N-t-butoxycarbonyl-2-(3-acetamido-4-hydroxyphenyl)glycine and N-t-butoxycarbonyl-2-(3-acetamido-2-hydroxyphenyl)glycine, was chromatographed on silica gel with 3:1 methylene chloride-ethyl acetate containing 1% acetic acid followed by 2:1 ethyl acetate-acetone containing 1% acetic acid to effect separation of the compounds, m.p. 178°–179° (4-hydroxy isomer from tetrahydrofuran-hexane); m.p. 171°–172° (2-hydroxy isomer from ethyl acetate-hexane).

EXAMPLE 25

α-(N-t-Butoxycarbonylamino)indole-3-acetic acid

A solution of 20.2 g. (0.070 mol.) of N-t-butoxycarbonyl-2-acetoxyglycine n-butyl ester and 8.8 g. (0.075 mol.) of indole in 300 ml. of toluene was slowly distilled over a 30 minutes interval with periodic replacement of the toluene with fresh solvent. After an additional 45 minutes the reaction mixture was cooled and the solvent was evaporated in vacuo. The residue was triturated with hexane to give α-(N-t-butoxycarbonylamino)indole-3-acetic acid n-butyl ester, m.p. 127°–128° (ether-hexane).

A suspension of 5.9 g. (0.017 mol.) of the ester in 70 ml. of 5% aqueous sodium carbonate and 30 ml. of dioxane was refluxed for 2.5 hours. The cooled reaction mixture was concentrated in vacuo and 30 ml. of water was added to the residue. The aqueous solution was extracted with methylene chloride, cooled and acidified to pH 2.0 with hydrochloric acid. The resulting solid was collected and recrystallized from ethyl acetate-hexane to give the title compound, m.p. 143.5°.

EXAMPLE 26

α-(N-t-butoxycarbonylamino)purine-7-acetic acid n-butyl ester and
α-(N-t-butoxycarbonylamino)-9H-purine-9-acetic acid n-butyl ester A mixture of 2.9 g. (0.01 mol.) of N-t-butoxycarbonyl-2-acetoxyglycine n-butyl ester and 1.2 g. (0.012 mol.) of purine was stirred under vacuum at 150°–160° until cessation of acetic acid evolution.

The cooled reaction mixture was taken up in 20 ml. of methylene chloride and the solution was filtered. Chromatography of the filtrate, containing a mixture of the title compounds, on 120 g. of silica gel with methylene chloride containing increasing amounts of acetone gave α-(N-t-butoxycarbonylamino)purine-7-acetic acid, m.p. 135°–136° (acetone) and α-(N-t-butoxycarbonylamino)-9H-purine-9-acetic acid, m.p. 164°–165° (acetone).

EXAMPLE 27

α-(N-t-Butoxycarbonylamino)furan-2-acetic acid n-butyl ester

A solution of 1.6 g. (0.006 mol.) of N-t-butoxycarbonyl-2-acetoxyglycine n-butyl ester and 0.7 g. (0.01 mol.) of redistilled furan in 75 ml. of methylene chloride was cooled to −78° and 4 drops of boron trifluoride etherate was added with stirring. The reaction mixture was warmed to room temperature and left for 3 hours Chromatography on silica gel with methylene chloride and methylene chloride containing increasing amounts of ethyl acetate gave the title compound.

EXAMPLE 28

N-t-Butoxycarbonyl-2-(4-hydroxyphenyl)glycine and
N-t-butoxycarbonyl-2-(2-hydroxyphenyl)glycine A solution of 1.5 g. (0.005 mol.) of N-t-butoxycarbonyl-2-acetoxyglycine n-butyl ester in 10 ml. of methylene chloride was slowly added over a 1 hour period to a stirred solution of 0.6 g. (0.006 mol.) of phenol and 0.1 ml. of boron trifluoride etherate in 15 ml. of methylene chloride. After 3 hours the reaction mixture was chromatographed on 50 g. of silica gel and eluted with methylene chloride containing increasing amounts of ethyl acetate to give N-t-butoxycarbonyl-2-(4-hydroxyphenyl)glycine n-butyl ester and N-t-butoxycarbonyl-2-(2-hydroxyphenyl)glycine n-butyl ester.

A solution of 0.5 g. (1.5 mmol.) of N-t-butoxycarbonyl-2-(4-hydroxyphenyl)glycine n-butyl ester in 20 ml. of methanol and 30 ml. of 5% aqueous sodium carbonate was heated at reflux for 30 minutes. The solvent was removed in vacuo and the aqueous residue was extracted with ethyl acetate. The aqueous phase was acidified to pH 3.0 with phosphoric acid and again extracted with ethyl acetate. The extract was dried (Na$_2$SO$_4$) and concentrated to give N-t-butoxycarbonyl-2-(4-hydroxyphenyl)glycine, m.p. 112°–114° (methanol-water).

Similarly, N-t-butoxycarbonyl-2-(2-hydroxyphenyl)glycine n-butyl ester was hydrolyzed to give N-t-butoxycarbonyl-2-(2-hydroxyphenyl)glycine, m.p. 125° (methylene chloride-water).

EXAMPLE 29

α-(N-t-Butoxycarbonylamino)pyrrole-2-acetic acid n-butyl ester

A solution of 14.5 g. (0.05 mol.) of N-t-butoxycarbonyl-2-acetoxyglycine n-butyl ester and 10 ml. of redistilled pyrrole in 75 ml. of toluene was slowly distilled with replacement of fresh toluene to maintain the volume at 50–75 ml. After 30 minutes the reaction mixture was cooled and concentrated in vacuo. The residue was dissolved in hexane and chromatographed on alumina (Woelm, activity II) with hexane-benzene followed by benzene to give the title compound.

EXAMPLE 30

N-Benzyloxycarbonyl-2-(4-hydroxyphenyl)glycine and N-benzyloxycarbonyl-2-(2-hydroxyphenyl)glycine To a solution of 1.73 g. (0.010 mol.) of phenol and 0.2 ml. of boron trifluoride etherate in 20 ml. of methylene chloride was added dropwise with stirring over a 15 minute interval 3.37 g. (0.011 mol.) of N-benzyloxycarbonyl-2-acetoxyglycine n-butyl ester. After three hours the reaction mixture was cooled and the precipitate collected by filtration to give N-benzyloxycarbonyl-2-(4-hydroxyphenyl)glycine n-butyl ester, m.p. 143°–144°.

The filtrate was concentrated in vacuo and the residue was dissolved in benzene and chromatographed on silica gel. Elution with benzene containing increasing amounts of ethyl acetate gave N-benzyloxycarbonyl-2-(2-hydroxyphenyl)glycine n-butyl ester, m.p. 114°–117° (ethyl acetate-hexane) and additional amounts of the 4-hydroxy isomer.

By the same procedure, substitution of an equivalent amount of N-benzyloxycarbonyl-2-n-butoxyglycine n-butyl ester for N-benzyloxycarbonyl-2-acetoxyglycine n-butyl ester gave N-benzyloxycarbonyl-2-(4-hydroxyphenyl)glycine n-butyl ester and N-benzyloxycarbonyl-2-(2-hydroxyphenyl)glycine n-butyl ester.

Hydrolysis of N-benzyloxycarbonyl-2-(4-hydroxyphenyl)glycine n-butyl ester as described in Example 29 gave N-benzyloxycarbonyl-2-(4-hydroxyphenyl)glycine, m.p. 188°–190° (dec.).

Similarly, N-benzyloxycarbonyl-2-(2-hydroxyphenyl)glycine n-butyl ester was hydrolyzed to give N-benzyloxycarbonyl-2-(2-hydroxyphenyl)glycine, m.p. 145°–148° (dec.).

N-Benzyloxycarbonyl-2-(4-hydroxyphenyl)glycine was also obtained from treatment of a cold solution of 3.3 g. (0.01 mol.) of N-benzyloxycarbonyl-2-S-benzylthioglycine and 1.9 g. (0.02 mol.) of phenol in 20 ml. of methylene chloride with 1 ml. of boron trifluoride etherate and 6.4 g (0.02 mol.) of mercuric acetate. The reaction mixture was stirred at 25° for 18 hours, then hydrogen sulfide was added to decompose the mercuric salts and the mixture was shaken with 5% aqueous sodium bicarbonate-ether. The aqueous phase was acidified to pH 2.0 with 5% hydrochloric acid and extracted with ethyl acetate. The extract was washed with water, dried ($Na_2SO_4$) and concentrated in vacuo to give N-benzyloxycarbonyl-2-(4-hydroxyphenyl)glycine, crystallized from ethyl acetate-hexane; m.p. 182°–185° (dec.).

EXAMPLE 31

N-Benzyloxycarbonyl-2-(4-methoxyphenyl)glycine n-butyl ester

When an equivalent amount of N-benzyloxycarbonyl-2-acetoxyglycine n-butyl ester was substituted in the procedure of Example 22 for N-t-butoxycarbonyl-2-acetoxy glycine n-butyl ester, the title compound was obtained.

EXAMPLE 32

N-Benzyloxycarbonyl-2-(4-methylthiophenyl)glycine n-butyl ester

A solution of 1.6 g. (5.0 mmol.) of N-benzyloxycarbonyl-2-acetoxyglycine n-butyl ester, 1.0 g. (8.0 mmol.) of thioanisole and 10 drops of boron trifluoride etherate in 10 ml. of methylene chloride was stirred at 25° for 2 hours. The reaction mixture was diluted with hexane and chromatographed on silica gel with hexane followed by 1:1 chloroform-hexane to give the title compound.

EXAMPLE 33

α-(N-Benzyloxycarbonylamino)thiophene-2-acetic acid n-butyl ester

A solution of 1.6 g. (5.0 mmol.) of N-benzyloxycarbonyl-2-acetoxyglycine n-butyl ester and 1.0 ml. of thiophene in 10 ml. of methylene chloride was treated with three drops of boron trifluoride etherate and left to stir at 25° for 16 hours. The reaction mixture was concentrated in vacuo and the residue was dissolved in methylene chloride and chromatographed on silica gel with methylene chloride containing increasing amounts of ethyl acetate to give the title compound, m.p. 37°.

EXAMPLE 34

α-(N-Benzyloxycarbonylamino)pyrrole-2-acetic acid n-butyl ester

Substitution of an equivalent amount of N-benzyloxycarbonyl-2-acetoxyglycine n-butyl ester in the procedure of Example 29 for N-t-butoxycarbonyl-2-acetoxyglycine n-butyl ester gave the title compound.

EXAMPLE 35

N-($\beta,\beta,\beta$-Trichloroethoxycarbonyl)-2-(4-methoxyphenyl)glycine n-butyl ester A solution of 0.91 g. (3.0 mmol.) of N-($\beta,\beta,\beta$-trichloroethoxycarbonyl)-2-acetoxyglycine n-butyl ester and 0.3 g. (2.8 mmol.) of anisole in 20 ml. of methylene chloride containing two drops of boron trifluoride etherate was maintained at 25° for 5 hours. The solvent was then evaporated in vacuo and 2:1 hexane-methylene chloride was added. Chromatography on silica gel with methylene chloride containing increasing amounts of ethyl acetate gave the title compound.

Alternatively, the title compound was obtained by substitution of 10 ml. of toluene containing 0.3 ml. of trifluoroacetic acid in the procedure described above for methylene chloride and boron trifluoride etherate followed by refluxing the reaction mixture for 1.75 hours and chromatography as described.

EXAMPLE 36

N-($\beta,\beta,\beta$-Trichloroethoxycarbonyl)-2-(4-hydroxy-3,5-dimethylphenyl)glycine n-butyl ester A solution of 1.8 g. (6 mmol.) of N-($\beta,\beta,\beta$-trichloroethoxycarbonyl)-2-acetoxyglycine n-butyl ester and 1.2 g. (10 mmol.) of 2,6-dimethylphenol in 20 ml. of methylene chloride containing 3 drops of boron trifluoride etherate was stirred at 25° for 3 hours. The reaction mixture was concentrated in vacuo, 5 ml. of 2:1 hexanemethylene chloride was added and the resulting solution was chromatographed on silica gel. Elution with 2:1 hexanemethylene chloride then with methylene chloride containing increasing amounts of ethyl acetate gave the title compound.

In like manner, the title compound was prepared by substituting an equivalent amount of formic acid or trifluoroacetic acid in the procedure above for methylene chloride and boron trifluoride etherate followed by refluxing the reaction mixture for one hour and chromatography as described.

EXAMPLE 37

α-(N-β,β,β-Trichloroethoxycarbonyl)pyrrole-2-acetic acid

When an equivalent amount of N-(β,β,β-Trichloroethoxycarbonyl)-2-acetoxyglycine n-butyl ester was substituted in the procedure of Example 29 for N-t-butoxycarbonyl-2-acetoxyglycine n-butyl ester, α-(β,β,β-trichloroethoxycarbonylamino)pyrrole-2-acetic acid n-butyl ester, m.p. 51.5° (hexane) was obtained.

A suspension of 3.7 g. of the ester in 5% aqueous sodium bicarbonate and 200 ml. of methanol was stirred at 25° for 48 hours. The reaction mixture was concentrated in vacuo and the remaining aqueous solution was extracted with methylene chloride. The aqueous phase was cooled acidified to pH 3.0 with phosphoric acid and extracted with ethyl acetate. The extract was dried ($Na_2SO_4$) and concentrated to give the title compound, m.p. 111° (hexane).

EXAMPLE 38

α-(N-β,β,β-Trichloroethoxycarbonylamino)purine-7-acetic acid n-butyl ester

When an equivalent amount of N-(β,β,β-trichloroethoxycarbonyl)-2-acetoxyglycine n-butyl ester was substituted in the procedure of Example 26 for N-t-butoxycarbonyl-2-acetoxyglycine n-butyl ester, the title compound was ultimately obtained, m.p. 114°–116° (major product; acetone-hexane).

We claim:
1. A process for preparing a compound of the formula:

where:
R¹ is lower alkyl of one to four carbon atoms, β,β,β-trichloroethyl, benzyl, p-nitrobenzyl or p-methoxybenzyl;
Y is O or S;
Ar is an aromatic or heteroaromatic group; and
R² is hydrogen or an easily-removable carboxyl protective group
comprising reacting a compound of the formula:

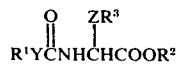

where:
R¹, Y and R² are as defined above;
Z is

and
R³ is lower alkyl of one to four carbon atoms, phenyl or benzyl, the phenyl or benzyl group being unsubstituted or substituted with one or two lower alkyl, lower alkoxy, hydroxy, halo, nitro, amino or acetamido groups
with a compound having an aromatic or heteroaromatic group capable of replacing said ZR³ group.

2. A process according to claim 1, where the compound having an aromatic or heteroaromatic group is phenyl lithium, anisole, resorcinol, 2-acetamidophenol, indole, purine, furan, phenol, chlorophenol, fluorophenol, pyrrole, thioanisole, thiophene or 2,6-dimethylphenol; R¹Y is t-butoxy, β,β,β-trichloroethoxy, benzyloxy, p-nitrobenzyloxy or p-methoxybenzyloxy; ZR³ is lower alkanoyloxy and R² is lower alkyl, β,β,β-trichloroethyl, benzyl, p-nitrobenzyl, p-methoxybenzyl, or hydrogen.

3. A process according to claim 2, where the reaction is acid-catalyzed.

4. A process according to claim 2, where ZR³ is acetoxy and R¹Y is t-butoxy or benzyloxy.

5. A process according to claim 2, where phenyl lithium is the compound having an aromatic or heteroaromatic group and ZR³ is acetoxy.

6. A process according to claim 3, where phenol is the compound having an aromatic or heteroaromatic group, ZR³ is acetoxy and the reaction is catalyzed by boron trifluoride etherate.

7. A process according to claim 1 where Ar is an aromatic group.

8. A process according to claim 7 where the compound having an aromatic group is phenol, resorcinol, 2-acetamidophenol, chlorophenol, fluorophenol or 2,6-dimethylphenol.

* * * * *

UNITED STATES PATENT AND TRADEMARK OFFICE
CERTIFICATE OF CORRECTION

PATENT NO. : 3,994,954
DATED : November 30, 1976
INVENTOR(S) : John G. Gleason, Kenneth G. Holden and Nelson C.F. Yim It is certified that error appears in the above—identified patent and that said Letters Patent are hereby corrected as shown below:

Structure IV in column 3 should appear as follows:

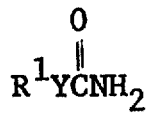

Column 13, lines 1 and 2, the title of Example 37 should read
-- α-(N-β,β,β-Trichloroethoxycarbonylamino)pyrrole-2-acetic acid -- .

Signed and Sealed this

Eighth Day of February 1977

[SEAL]

Attest:

RUTH C. MASON
*Attesting Officer*

C. MARSHALL DANN
*Commissioner of Patents and Trademarks*